(12) United States Patent
Hamer

(10) Patent No.: US 11,417,419 B1
(45) Date of Patent: Aug. 16, 2022

(54) FACILITATING ACCESS TO PATIENT MEDICAL INFORMATION

(71) Applicant: Allscripts Software, LLC, Raleigh, NC (US)

(72) Inventor: Andre Hamer, Petah Tikva (IL)

( * ) Notice: Subject to any disclaimer, the term of this patent is extended or adjusted under 35 U.S.C. 154(b) by 804 days.

(21) Appl. No.: 16/375,688

(22) Filed: Apr. 4, 2019

Related U.S. Application Data

(63) Continuation of application No. 14/872,115, filed on Sep. 30, 2015, now Pat. No. 10,276,262.

(51) Int. Cl.
    *G16H 10/60*     (2018.01)
    *G16H 50/70*     (2018.01)

(52) U.S. Cl.
    CPC .............. *G16H 10/60* (2018.01); *G16H 50/70* (2018.01)

(58) Field of Classification Search
None
See application file for complete search history.

(56) References Cited

U.S. PATENT DOCUMENTS

| | | | |
|---|---|---|---|
| 8,145,716 B2 | 3/2012 | Karamchedu et al. | |
| 2004/0054744 A1 | 3/2004 | Karamchedu et al. | |
| 2005/0261011 A1* | 11/2005 | Scott | G06Q 10/10 455/466 |
| 2006/0092920 A1 | 5/2006 | Karamchedu et al. | |
| 2009/0083664 A1 | 3/2009 | Bay et al. | |
| 2010/0057732 A1* | 3/2010 | O'Sullivan | G06Q 30/02 709/206 |
| 2011/0026778 A1* | 2/2011 | Ye | G06F 16/583 382/118 |
| 2012/0078654 A1* | 3/2012 | DeGruttola | G06Q 10/109 705/2 |
| 2013/0047113 A1 | 2/2013 | Hume et al. | |
| 2013/0073306 A1 | 3/2013 | Shlain et al. | |

(Continued)

OTHER PUBLICATIONS

Voicegio debuts click-to-call feature; new option allows GloPhone and GloConnect users to make internet calls in one simple click. (Jan. 11, 2005). Business Wire Retrieved from https://dialog.proquest.com/professional/docview/445510935?accountid=131444 (Year: 2005).*

(Continued)

*Primary Examiner* — Robert A Sorey
(74) *Attorney, Agent, or Firm* — Calfee, Halter & Griswold LLP

(57) ABSTRACT

A method includes displaying a window of a first application which includes text corresponding to a patient identifier for a first patient. The method further includes receiving input corresponding to a preconfigured input sequence associated with an electronic health records (EHR) agent, and initiating, by the EHR agent in response to the preconfigured input sequence, a patient information overlay process. The patient information overlay process includes sending a copy command to copy first text from the window of the first application to the clipboard, accessing the first text, searching the accessed first text for an identification of a patient, determining that the patient identifier represents an identification of a patient, accessing patient information for the first patient based on the patient identifier, and displaying an overlay interface overlaid over the window proximate a cursor, the overlay interface including accessed patient information for the first patient.

20 Claims, 6 Drawing Sheets

(56) References Cited

U.S. PATENT DOCUMENTS

| | | |
|---|---|---|
| 2014/0280353 A1 | 9/2014 | Delaney et al. |
| 2014/0321773 A1 | 10/2014 | Hammon et al. |
| 2015/0012887 A1 | 1/2015 | Ash et al. |
| 2015/0195220 A1* | 7/2015 | Hawker .................. H04L 51/16 707/723 |
| 2015/0356647 A1 | 12/2015 | Reiser et al. |
| 2016/0171538 A1* | 6/2016 | Balasubramanian ........................ G06Q 30/0255 705/14.53 |
| 2016/0203281 A1 | 7/2016 | Zalis et al. |

OTHER PUBLICATIONS

"Non-Final Office Action for U.S. Appl. No. 14/872,115", dated Mar. 23, 2018, 9 pages.
"Response to the Non-Final Office Action for U.S. Appl. No. 14/872,115", Filed Date: Jul. 23, 2018, 12 pages.
"Notice of Allowance and Fees Due for U.S. Appl. No. 14/872,115", dated Dec. 19, 2018, 9 pages.

* cited by examiner

FACILITATING ACCESS TO PATIENT MEDICAL INFORMATION

RELATED APPLICATION

This application is a continuation of U.S. patent application Ser. No. 14/872,115, filed on Sep. 30, 2015, and entitled "FACILITATING ACCESS TO PATIENT MEDICAL INFORMATION". The aforementioned application is incorporated in its entirety herein by reference.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention generally relates to accessing patient medical information.

Traditionally, a healthcare practitioner accesses patient medical data by logging in to an electronic health records (EHR) application, searching for a patient, and then opening medical information for that patient. If a healthcare practitioner runs across a reference to a patient in a document outside of the EHR application, such as an email, chat message, or PDF document, the practitioner generally needs to return to the EHR application and search for the patient in order to access the patient's medical information.

A need exists for improvement in accessing patient medical information. This need and other needs are addressed by one or more aspects of the present invention.

SUMMARY OF THE INVENTION

The present invention includes many aspects and features. Moreover, while many aspects and features relate to, and are described in, a particular context, the present invention is not limited to use only in this context, as will become apparent from the following summaries and detailed descriptions of aspects, features, and one or more embodiments of the present invention.

Accordingly, one aspect of the present invention relates to a method comprising displaying, to a user via a display associated with an electronic device, a window of a first application, the window including text corresponding to a patient identifier for a first patient; receiving, from the user via a mouse associated with the electronic device, input corresponding to positioning of a cursor over the text corresponding to a patient identifier; receiving, from the user via the mouse and a keyboard associated with the electronic device, input corresponding to a preconfigured input sequence associated with an electronic health records (EHR) agent; initiating, by the EHR agent in response to the preconfigured input sequence, a patient information overlay process; sending, by the EHR agent as part of the patient information overlay process, a copy command to copy first text from the window of the first application to the clipboard; accessing, by the EHR agent from the clipboard as part of the patient information overlay process, the first text; searching, by the EHR agent as part of the patient information overlay process, the accessed first text for an identification of a patient, and determining that the patient identifier represents an identification of a patient; accessing, by the EHR agent as part of the patient information overlay process, patient information for the first patient based on the patient identifier; and displaying, to the user via the display associated with the electronic device, an overlay interface overlaid over the window proximate the cursor, the overlay interface including accessed patient information for the first patient.

In a feature of this aspect, the first application comprises an email application.

In a feature of this aspect, the first application comprises a messaging application.

In a feature of this aspect, the first application comprises a word processing application.

In a feature of this aspect, the first application comprises a PDF application.

In a feature of this aspect, the first application comprises a slideshow application.

In a feature of this aspect, the first application comprises a video conferencing application.

In a feature of this aspect, the first application comprises a browser application.

In a feature of this aspect, the method further comprises receiving, from the user via a mouse associated with the electronic device, input corresponding to movement of the cursor a certain distance away from the overlay interface; effecting, by the EHR agent in response to the movement of the cursor a certain distance away from the overlay interface, fading out of the overlay interface.

Another aspect relates to a method comprising displaying, to a user via a display associated with an electronic device, a window of a first application, the window including text corresponding to a patient identifier for a first patient; receiving, from the user via a mouse associated with the electronic device, input corresponding to positioning of a cursor over the text corresponding to a patient identifier; receiving, from the user via the mouse and a keyboard associated with the electronic device, input corresponding to a preconfigured input sequence associated with an electronic health records (EHR) agent; initiating, by the EHR agent in response to the preconfigured input sequence, a patient information overlay process; accessing, by the EHR agent as part of the patient information overlay process, first text from the window of the first application utilizing an application programming interface for the first application; searching, by the EHR agent as part of the patient information overlay process, the accessed first text for an identification of a patient, and determining that the patient identifier represents an identification of a patient; accessing, by the EHR agent as part of the patient information overlay process, patient information for the first patient based on the patient identifier; and displaying, to the user via the display associated with the electronic device, an overlay interface overlaid over the window proximate the cursor, the overlay interface including accessed patient information for the first patient.

In a feature of this aspect, the first application comprises an email application.

In a feature of this aspect, the first application comprises a messaging application.

In a feature of this aspect, the first application comprises a word processing application.

In a feature of this aspect, the first application comprises a PDF application.

In a feature of this aspect, the first application comprises a slideshow application.

In a feature of this aspect, the first application comprises a video conferencing application.

In a feature of this aspect, the first application comprises a browser application.

In a feature of this aspect, the method further comprises receiving, from the user via a mouse associated with the electronic device, input corresponding to movement of the cursor a certain distance away from the overlay interface; and effecting, by the EHR agent in response to the movement of the cursor a certain distance away from the overlay interface, fading out of the overlay interface.

Another aspect relates to a method comprising displaying, to a user via a display associated with an electronic device, a window of a first application, the window including text corresponding to a patient identifier for a first patient; receiving, from the user via a mouse associated with the electronic device, input corresponding to positioning of a cursor over the text corresponding to a patient identifier; receiving, from the user via the mouse and a keyboard associated with the electronic device, input corresponding to a preconfigured input sequence associated with an electronic health records (EHR) agent; initiating, by the EHR agent in response to the preconfigured input sequence, a patient information overlay process; programmatically accessing, by the EHR agent as part of the patient information overlay process, an interface element of the first application corresponding to the window, and accessing first text from the window of the first application utilizing the accessed interface element of the first application; searching, by the EHR agent as part of the patient information overlay process, the accessed first text for an identification of a patient, and determining that the patient identifier represents an identification of a patient; accessing, by the EHR agent as part of the patient information overlay process, patient information for the first patient based on the patient identifier; and displaying, to the user via the display associated with the electronic device, an overlay interface overlaid over the window proximate the cursor, the overlay interface including accessed patient information for the first patient.

In a feature of this aspect, the method further comprises receiving, from the user via a mouse associated with the electronic device, input corresponding to movement of the cursor a certain distance away from the overlay interface; effecting, by the EHR agent in response to the movement of the cursor a certain distance away from the overlay interface, fading out of the overlay interface.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings, wherein the same elements are referred to with the same reference numerals, and wherein.

DETAILED DESCRIPTION

Figure 1:
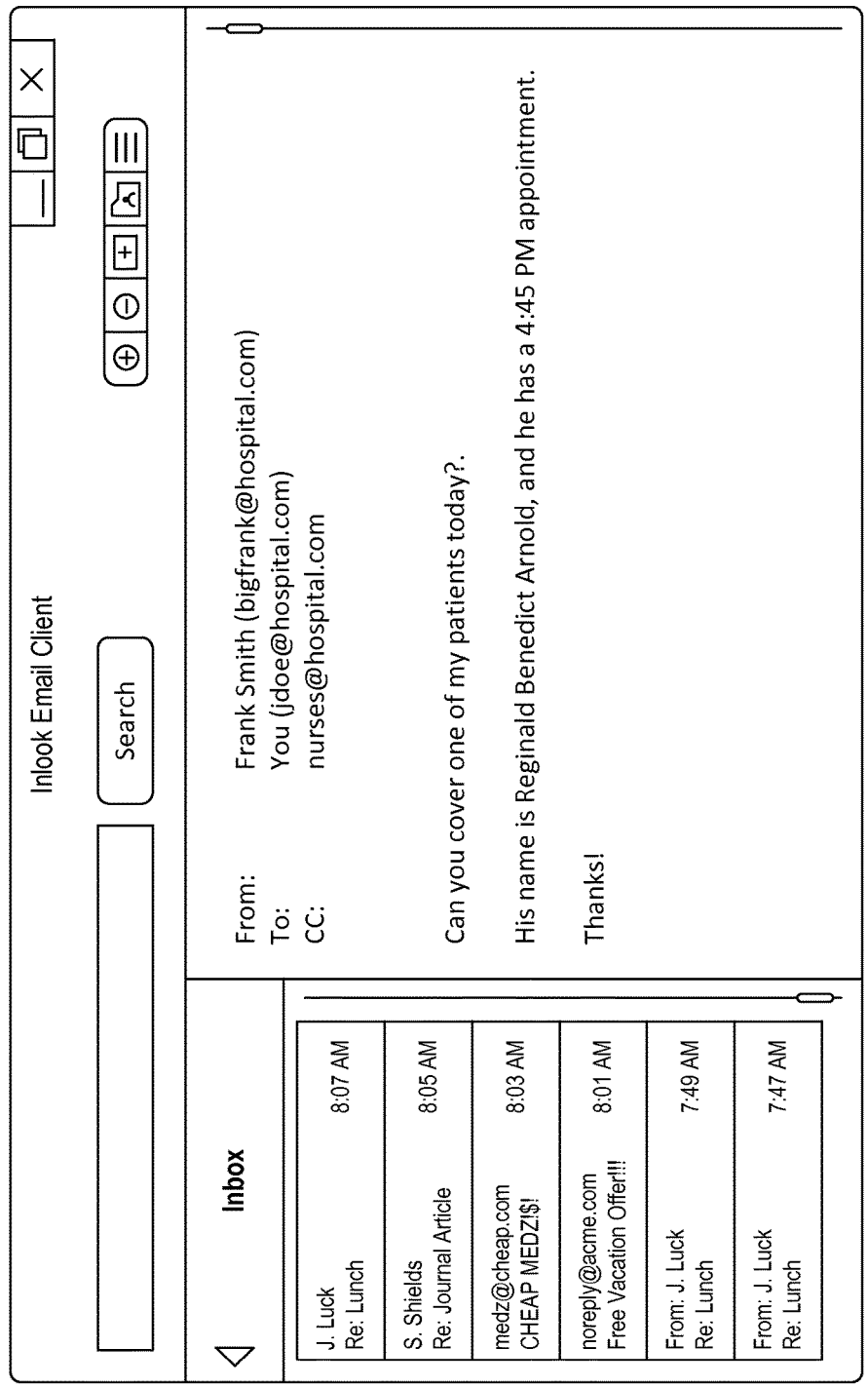
FIGS. 1-3 illustrate use of a preferred implementation with an exemplary email application in which a user has received an email containing a patient's name.

As a preliminary matter, it will readily be understood by one having ordinary skill in the relevant art ("Ordinary Artisan") that the invention has broad utility and application. Furthermore, any embodiment discussed and identified as being "preferred" is considered to be part of a best mode contemplated for carrying out the invention. Other embodiments also may be discussed for additional illustrative purposes in providing a full and enabling disclosure of the invention. Furthermore, an embodiment of the invention may incorporate only one or a plurality of the aspects of the invention disclosed herein; only one or a plurality of the features disclosed herein; or combination thereof. As such, many embodiments are implicitly disclosed herein and fall within the scope of what is regarded as the invention.

Accordingly, while the invention is described herein in detail in relation to one or more embodiments, it is to be understood that this disclosure is illustrative and exemplary of the invention, and is made merely for the purposes of providing a full and enabling disclosure of the invention. The detailed disclosure herein of one or more embodiments is not intended, nor is to be construed, to limit the scope of patent protection afforded the invention in any claim of a patent issuing here from, which scope is to be defined by the claims and the equivalents thereof. It is not intended that the scope of patent protection afforded the invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the invention. Accordingly, it is intended that the scope of patent protection afforded the invention is to be defined by the issued claim(s) rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. 112, paragraph 6 or subsection (f), no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." When used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the invention are next described. The following description of one or more preferred embodiments is merely exemplary in nature and is in no way intended to limit the invention, its implementations, or uses.

In accordance with one or more preferred implementations, a system comprises an EHR agent which is designed to sit on top of existing EHR software in an EHR agnostic manner. Such a system is disclosed, for example, in U.S. Patent Application Pub. No. 2012/0215560, which patent application publication is hereby incorporated herein by reference. In accordance with one or more preferred implementations, a system aggregates data from a plurality of sources, including a plurality of EHR systems. In accordance with one or more preferred implementations, the system includes an EHR agent which comprises a graphical interface designed to overlay an EHR interface and provide information that may not be present in the EHR.

In accordance with one or more preferred implementations, an EHR agent intercepts context from an EHR application (such as a current patient for which data is being displayed), and uses such intercepted context to select data for display in an agent interface.

In accordance with one or more preferred implementations, an EHR agent is configured for use with EHR applications compliant with the clinical context object workgroup (CCOW) standard protocol. In accordance with one or more preferred implementations, an EHR agent utilizes one or more customized plugins or adapters to support use with EHR applications that are not compliant with the CCOW standard protocol.

In accordance with one or more preferred implementations, an EHR agent is configured for use with applications other than EHR applications as well. Specifically, in accordance with one or more preferred implementations, an EHR agent is configured to access and display patient information in an overlay interface in response to a specific input sequence from a user.

For example, in accordance with one or more preferred implementations, an EHR agent is configured to allow a user to hold down a particular key (such as control) and click or double click on text representing a patient identifier (such as a patient name, patient ID, or medical record number) in an application window to bring up an overlay interface of the EHR agent presenting information for that patient.

Figure 2:
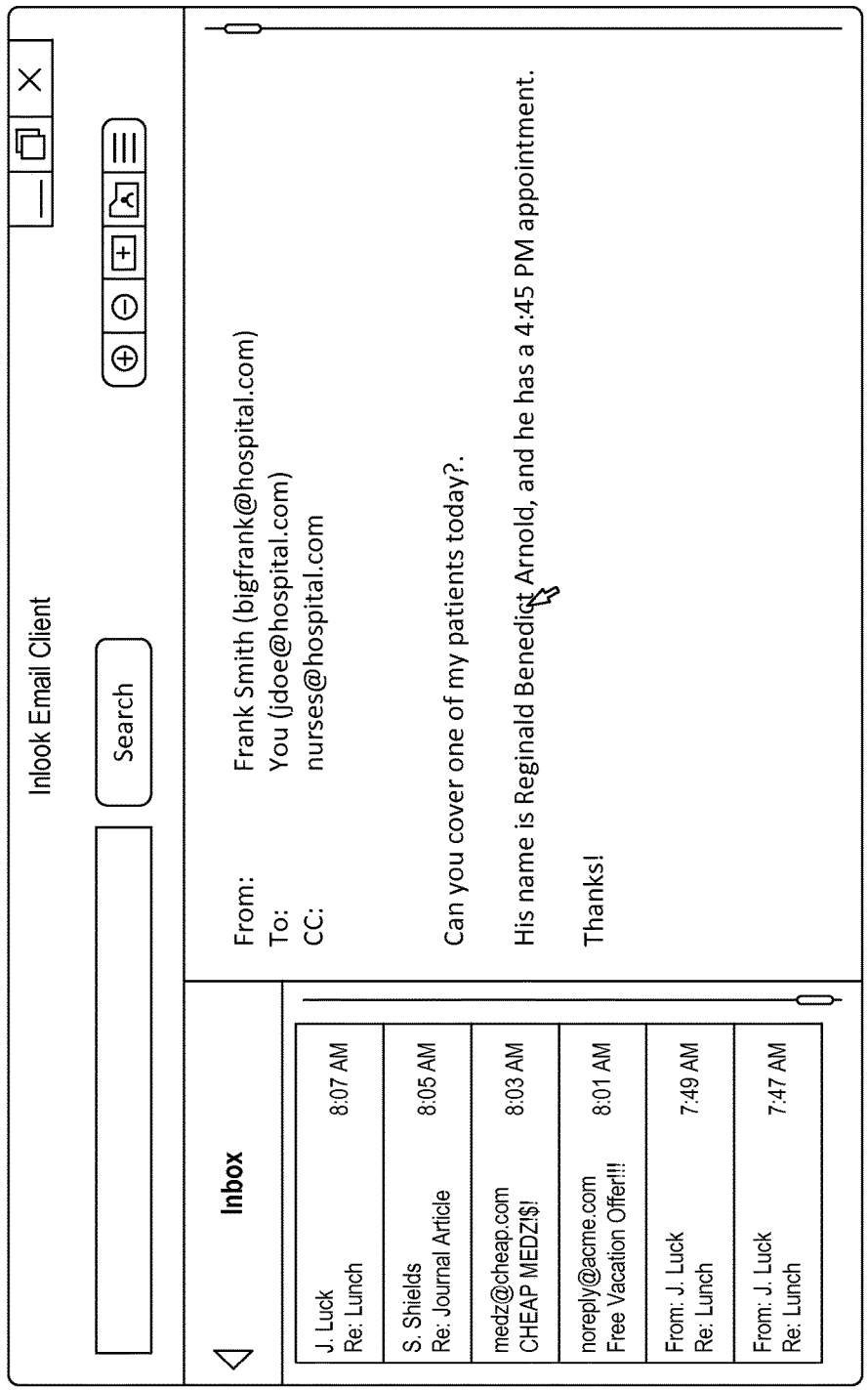
Figure 3:

FIG. 1 illustrates an exemplary email application in which a user has received an email containing a patient's name. In accordance with a preferred implementation, the user can hover his mouse over the patient's name, as illustrated in FIG. 2, hold down a particular key (e.g. the control key) and perform one or more clicks (e.g. a double click) to trigger the EHR agent to access patient health information for that patient and display it an overlay, as illustrated in FIG. 3. This overlay is preferably expandable for the display of additional health information, and/or provides access to a more detailed overlay or interface including additional health information. In accordance with one or more preferred implementations, the overlay is opened proximate a current cursor position.

Figure 4:
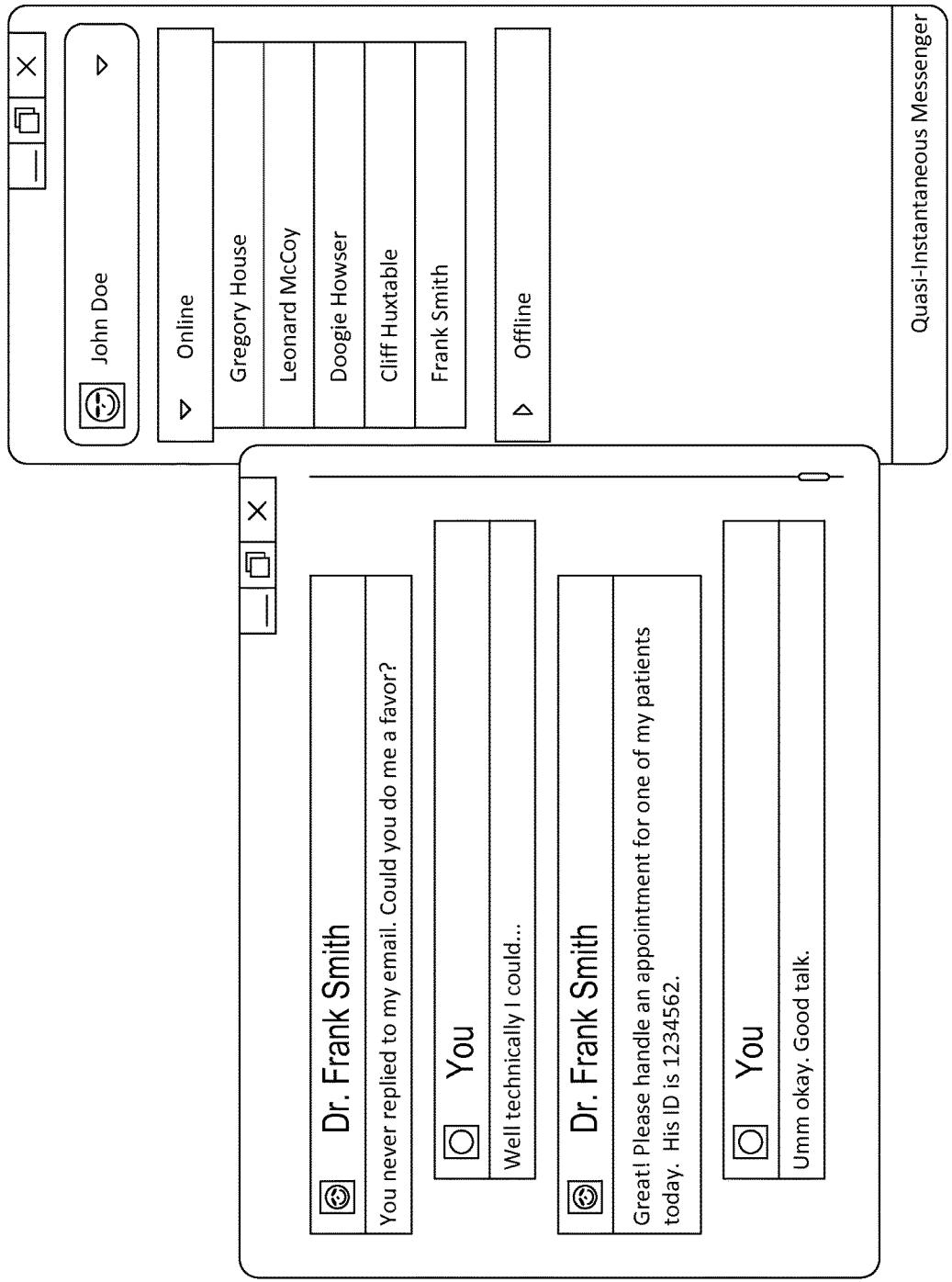
FIGS. 4-6 illustrate use of a preferred implementation with an exemplary messaging application in which a user has received a message containing a patient ID.
Figure 5:
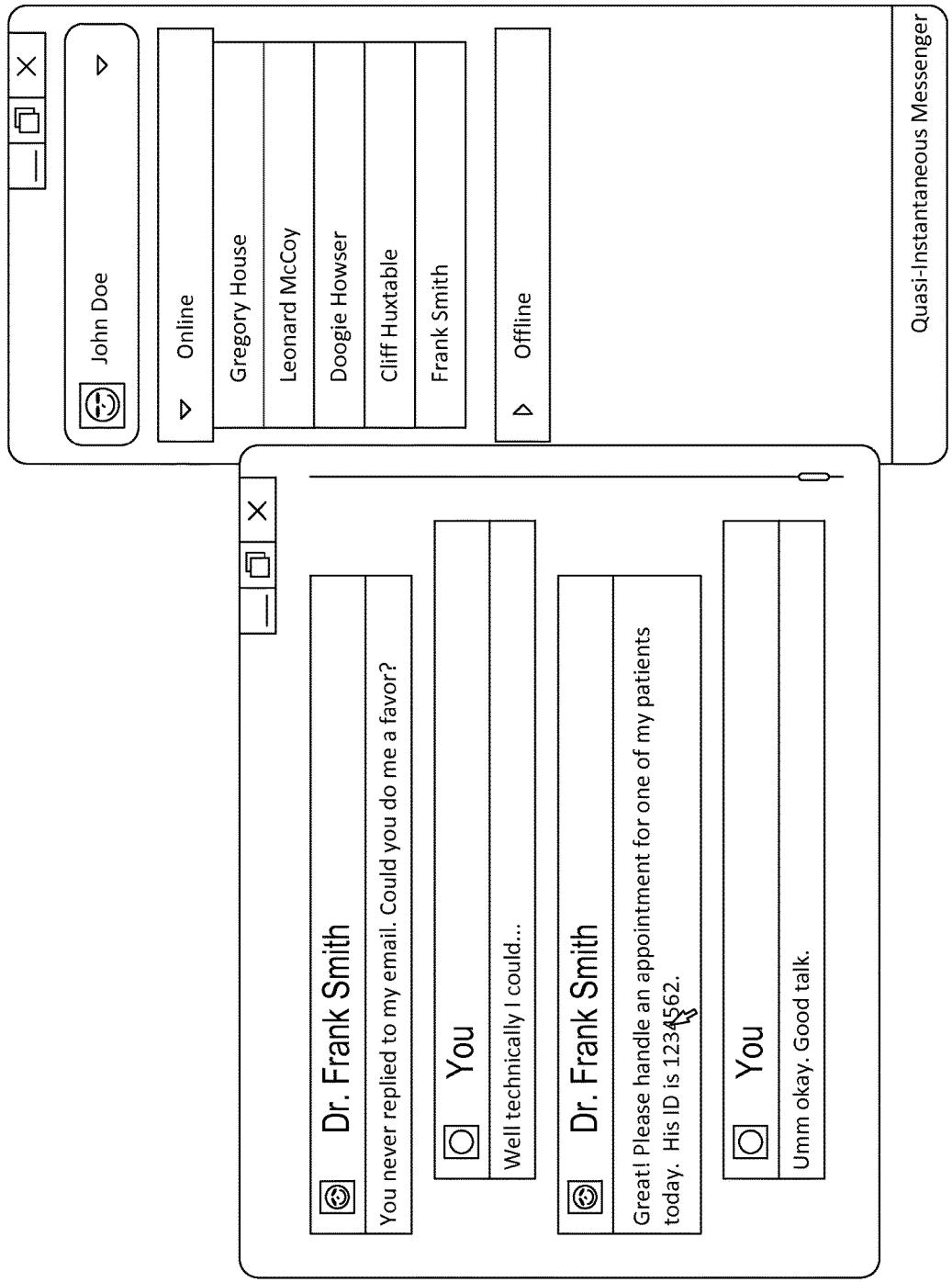
Figure 6:
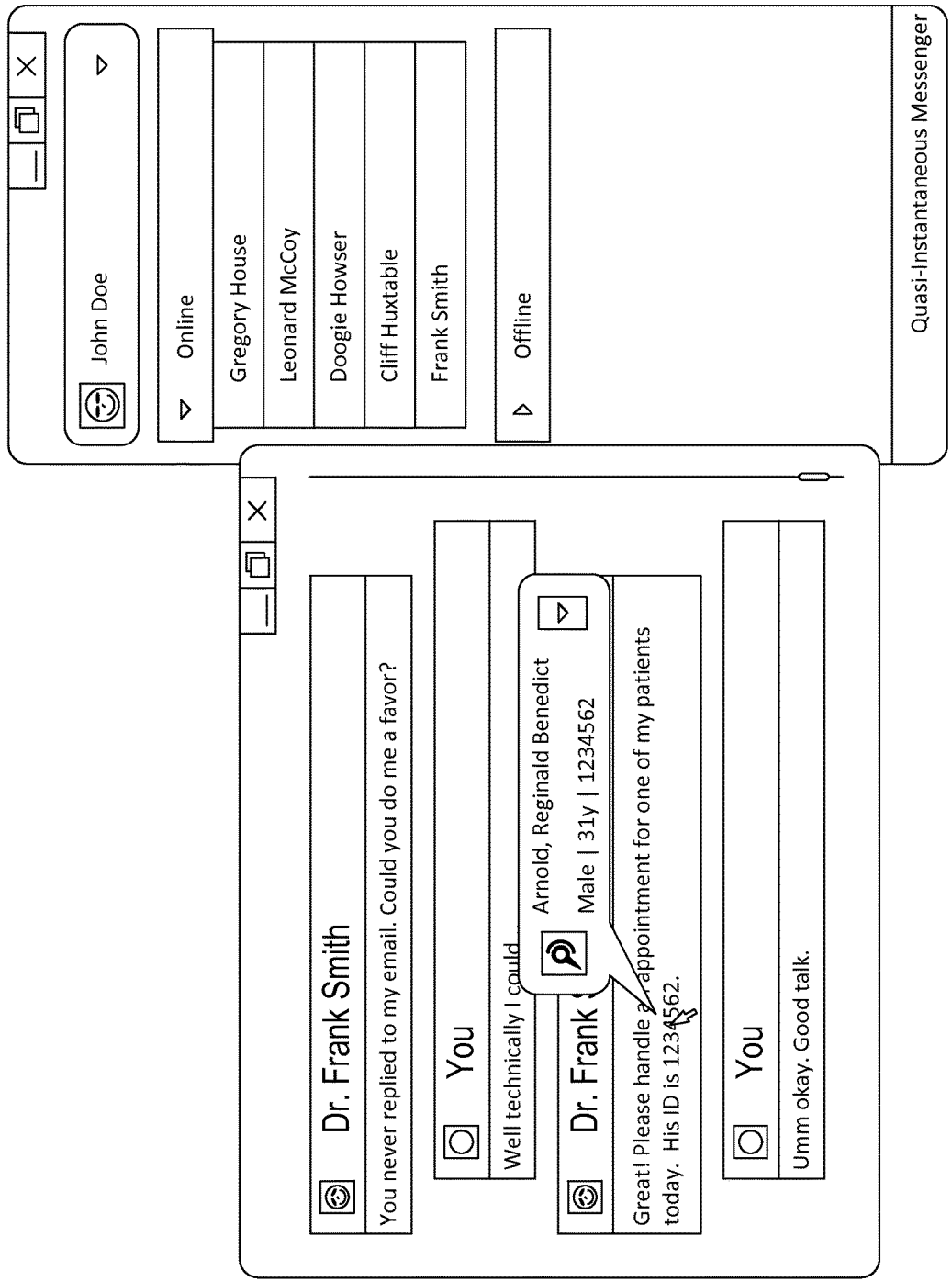

Notably, an email application is just one example of an application that the EHR agent can be utilized with. As another example, FIG. 4 illustrates an exemplary messaging application in which the user has received a follow up message from the same doctor regarding the same patient. In this case, however, the message includes a numerical patient ID rather than the patient's name. Similar to the previous example, the user can hover his mouse over the patient ID, as illustrated in FIG. 5, hold down a particular key (e.g. the control key) and perform one or more clicks (e.g. a double click) to trigger the EHR agent to access patient health information for that patient and display it an overlay, as illustrated in FIG. 6

In accordance with one or more preferred implementations, an EHR agent is configured to allow a user to customize an input sequence that triggers display of an overlay containing patient health information. For example, a user may be able to specify an input sequence of control+ double click, or shift+alt+single click, etc.

Email and messaging applications are just exemplary applications that an EHR agent can be utilized with. In accordance with one or more preferred implementations, an EHR agent is configured for use with browser applications (such as Internet Explorer, Firefox, and Chrome), notepad applications, word processing applications (such as Microsoft Word), spreadsheet applications (such as Microsoft Excel), slideshow applications (such as Microsoft PowerPoint), document applications (such as Adobe Acrobat), and conferencing applications (such as Skype).

In accordance with one or more preferred implementations, an EHR agent utilizes different approaches to gather patient context information from various applications, although in at least some preferred implementations, an EHR agent may utilize only a single approach for multiple applications.

In accordance with one or more preferred implementations, an EHR agent is configured to access a patient identifier from an application window for a particular application utilizing a specific application programming interface for that particular application. In accordance with one or more preferred implementations, this process involves determining an active application window and/or a cursor location relative to an active application window.

Additionally or alternatively, in accordance with one or more preferred implementations, an EHR agent is configured to access a patient identifier from an application window for a particular application by accessing or loading a user interface element of the particular application. In accordance with one or more preferred implementations, this process involves determining an active application window and/or a cursor location relative to an active application window.

Additionally or alternatively, in accordance with one or more preferred implementations, an EHR agent is configured to access a patient identifier from an application window for a particular application by sending a copy command (e.g. by simulating a control+c keyboard press) and copying text from the application window to the clipboard, and then accessing text from the clipboard and searching within it for a patient identifier.

In accordance with one or more preferred implementations, in order to obviate any potential patient safety issues caused by having patient information for multiple patients open or accessible at a given time, an overlay interface is configured to fade out after a user moves his or her mouse cursor away from the overlay interface.

In accordance with one or more preferred implementations, an EHR agent is configured for use with various operating systems, such as, for example, Microsoft Windows or Apple OS X.

Although described herein largely in the context of a computer having a mouse and keyboard, in accordance with one more preferred implementations, an EHR agent is configured for use with a mobile device such as a touchscreen device. In accordance with one or more preferred implementations, an EHR agent is configured for use with a tablet or smartphone.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A client computing device, comprising:
a processor;
a display; and
memory storing a client electronic health records (EHR) agent that, when executed by the processor, causes the processor to perform acts comprising:
receiving a patient identifier for a patient, wherein the patient identifier is received due to the patient identifier being displayed on the display in a window of an instant messaging application that is executing on the client computing device;
responsive to receiving the patient identifier, transmitting the patient identifier to a server EHR agent executing on a server computing device that is in network communication with the client computing device, wherein the server EHR agent retrieves patient information for the patient based upon the patient identifier, wherein the server EHR agent transmits the patient information to the client EHR agent; and
responsive to receiving the patient information from the server EHR agent, displaying an overlay interface on the display that is overlaid over the window of the instant messaging application, the overlay interface including the patient identifier and the patient information for the patient.

2. The client computing device of claim 1, wherein the overlay interface further includes a visual marker indicating that the patient information has been retrieved by the client EHR agent.

3. The client computing device of claim 1, wherein the server EHR agent retrieves the patient information via communication with an EHR application executing on a second server computing device, wherein the EHR application maintains the patient information.

4. The client computing device of claim 3, wherein the server EHR agent communicates with the EHR application via a clinical context object workgroup (CCOW) standard protocol.

5. The client computing device of claim 3, wherein the overlay interface further includes a dropdown button that indicates that actions performed by the EHR application with respect to the patient information are available.

6. The client computing device of claim 1, the acts further comprising:
detecting that the cursor has been moved a predefined distance away from the overlay interface; and
responsive to detecting that the cursor has been moved the predefined distance away from the overlay interface, fading out the overlay interface on the display.

7. The client computing device of claim 1, wherein the client EHR agent receives the patient identifier for the patient due to the client computing device receiving a preconfigured input sequence from a user of the client computing device.

8. A method performed by a processor of a client computing device while the processor executes a client electronic health records (EHR) agent, the method comprising:
receiving a patient identifier for a patient, wherein the patient identifier is received due to the patient identifier being displayed on a display of the client computing device in a window of an instant messaging application that is executing on the client computing device;
responsive to receiving the patient identifier, transmitting the patient identifier to a server EHR agent executing on a server computing device that is in network communication with the client computing device, wherein the server EHR agent retrieves patient information for the patient based upon the patient identifier, wherein the server EHR agent transmits the patient information to the client EHR agent; and
responsive to receiving the patient information from the server EHR agent, displaying an overlay interface on the display that is overlaid over the window of the instant messaging application, the overlay interface including the patient identifier and the patient information for the patient.

9. The method of claim 8, wherein the overlay interface further includes a visual marker indicating that the patient information has been retrieved by the client EHR agent.

10. The method of claim 8, wherein the server EHR agent retrieves the patient information via communication with an EHR application executing on a second server computing device, wherein the EHR application maintains the patient information.

11. The method of claim 10, wherein the server EHR agent communicates with the EHR application via a clinical context object workgroup (CCOW) standard protocol.

12. The method of claim 10, wherein the overlay interface further includes a dropdown button that indicates that actions performed by the EHR application with respect to the patient information are available.

13. The method of claim 8, further comprising:
detecting that the cursor has been moved a predefined distance away from the overlay interface; and responsive to detecting that the cursor has been moved the predefined distance away from the overlay interface, fading out the overlay interface on the display.

14. The method of claim 8, further comprising:
prior to receiving the preconfigured input sequence, wherein the client EHR agent receives the patient identifier by performing an application programming interface (API) call to the instant messaging application, thereby causing the instant messaging application to transmit the patient identifier to the client EHR agent.

15. A computer-readable storage medium that stores a client electronic health records (EHR) agent that, when executed by a processor of a client computing device, causes the processor to perform acts comprising:
receiving a patient identifier for a patient, wherein the patient identifier is received due to the patient identifier being displayed on a display of the client computing device in a window of an instant messaging application that is executing on the client computing device;
responsive to receiving the patient identifier, transmitting the patient identifier to a server EHR agent executing on a server computing device that is in network communication with the client computing device, wherein the server EHR agent retrieves patient information for the patient based upon the patient identifier, wherein the server EHR agent transmits the patient information to the client EHR agent; and
responsive to receiving the patient information from the server EHR agent, displaying an overlay interface on the display that is overlaid over the window of the instant messaging application, the overlay interface including the patient identifier and the patient information for the patient.

16. The computer-readable storage medium of claim 15, wherein the overlay interface further includes a visual marker indicating that the patient information has been retrieved by the client EHR agent.

17. The computer-readable storage medium of claim 15, wherein the server EHR agent retrieves the patient information via communication with an EHR application executing on a second server computing device, wherein the EHR application maintains the patient information.

18. The computer-readable storage medium of claim 17, wherein the server EHR agent communicates with the EHR application via a clinical context object workgroup (CCOW) standard protocol.

19. The computer-readable storage medium of claim 17, wherein the overlay interface further includes a dropdown button that indicates that actions performed by the EHR application with respect to the patient information are available.

20. The computer-readable storage medium of claim 15, the acts further comprising:
detecting that the cursor has been moved a predefined distance away from the overlay interface; and
responsive to detecting that the cursor has been moved the predefined distance away from the overlay interface, fading out the overlay interface on the display.

* * * * *